(12) United States Patent
Dykaar (10) Patent No.: US 11,426,070 B2
(45) Date of Patent: Aug. 30, 2022

(54) INFRARED ILLUMINATOR AND RELATED EYE TRACKING APPARATUS AND METHOD (71) Applicant: GOOGLE LLC, Mountain View, CA (US)

(72) Inventor: Douglas Raymond Dykaar, Waterloo (CA)

(73) Assignee: Google LLC, Mountain View, CA (US)

(*) Notice: Subject to any disclaimer, the term of this patent is extended or adjusted under 35 U.S.C. 154(b) by 194 days.

(21) Appl. No.: 16/699,263

(22) Filed: Nov. 29, 2019

(65) Prior Publication Data
US 2020/0170504 A1 Jun. 4, 2020

Related U.S. Application Data (60) Provisional application No. 62/773,855, filed on Nov. 30, 2018.

(51) Int. Cl.
A61B 3/14 (2006.01)
A61B 3/10 (2006.01)
A61B 3/00 (2006.01)
G03H 1/00 (2006.01)
G02B 27/14 (2006.01)
G03B 21/26 (2006.01)
A61B 3/113 (2006.01)
G02B 27/01 (2006.01)
G06F 3/01 (2006.01)

(52) U.S. Cl.
CPC .......... *A61B 3/113* (2013.01); *G02B 27/0172* (2013.01); *G06F 3/013* (2013.01)

(58) Field of Classification Search
CPC .......... G09G 3/003; A61B 3/103; A61B 3/14; A61B 3/113; A61B 3/1225; A61B 3/024; A61B 3/032; A61B 3/1015; G02C 5/00; G02B 27/0172; G02B 27/0149; G02B 27/145; G02B 27/0103; G02B 27/0101
USPC ....... 351/210, 200, 205, 206, 209, 221–223, 351/246, 41; 359/630–634, 13–14; 353/11–12, 28, 119
See application file for complete search history.

(56) References Cited

U.S. PATENT DOCUMENTS

| | | | |
|---|---|---|---|
| 2014/0354953 A1* | 12/2014 | Chen | A61B 3/113 351/210 |
| 2017/0330042 A1* | 11/2017 | Vaziri | G06K 9/00604 |
| 2020/0096772 A1* | 3/2020 | Adema | G02C 7/086 |

* cited by examiner

Primary Examiner — Dawayne Pinkney (57) ABSTRACT

An apparatus to illuminate a target includes a lens having a lens side to be positioned in opposing relation to the target. The apparatus includes a lightguide that circumscribes at least a portion of the periphery of the lens. The lightguide has an input end to receive light and a length along which the receive light propagates. The apparatus includes outcoupling elements that are spaced out along the length of the lightguide. The outcoupling elements couple light out of the lightguide at respective positions along the length of the lightguide. The outcoupling elements are oriented to direct the outcoupled light towards the target when the lens side is positioned in opposing relation to the target. An eye tracking apparatus including the illumination apparatus and a method of eye tracking are disclosed.

20 Claims, 9 Drawing Sheets

INFRARED ILLUMINATOR AND RELATED EYE TRACKING APPARATUS AND METHOD

CROSS-REFERENCE TO RELATED APPLICATIONS

This application claims the benefit of U.S. Provisional Application No. 62/773,855, filed 30 Nov. 2018, the disclosure of which is incorporated herein by reference.

TECHNICAL FIELD

The disclosure relates generally to methods and systems for tracking a gaze position of an eye in a target space, such as a display space formed by a wearable heads-up display, and particularly to illumination of an eye with infrared light.

BACKGROUND

Eye tracking is a process by which one or more of a position, orientation, and motion of an eye may be measured or monitored. In many applications, this is done with a view towards determining the gaze direction of a user. There are various eye tracking techniques, the least invasive of which employs one or more optical sensors, e.g., cameras, to optically track the eye. Common techniques involve illuminating or flooding the eye with infrared light and measuring reflections from the eye with at least one optical sensor that is tuned to be sensitive to the infrared light. Reflections of infrared light from the eye are analyzed to determine the position, orientation, and/or motion of one or more eye features, such as the cornea, pupil, iris, and/or retinal blood vessels.

Eye tracking may be implemented in near-eye or head-mounted devices that have a structure to deliver light to the eye. One example of such near-eye or head-mounted devices is a wearable heads-up display that can be worn on the head like conventional glasses. In wearable heads-up displays, eye tracking can enable a variety of functionalities, such as influencing where content is displayed in the field of view of the user, conserving power by not displaying content that is outside of the field of view of the user, influencing what content is displayed to the user, determining where the user is looking or gazing, determining whether the user is looking at displayed content on the display or at scenes in the external environment, and providing an interface through which the user may control or interact with displayed content.

One of the challenges of integrating eye tracking with a wearable heads-up display is placement of light sources to illuminate the eye with infrared light without making the wearable heads-up display bulky and/or without interfering with the ability of the wearable heads-up display to project images into the display space.

SUMMARY

In a first aspect, an apparatus to illuminate a target may be summarized as including a support frame that carries a lens and a lightguide. The lens has a lens side that is to be positioned in opposing relation to the target. The lightguide circumscribes at least a portion of the periphery of the lens and has an input end to receive light and a length along which the received light propagates. A plurality of outcoupling elements are spaced out along the length of the lightguide and optically coupled to the lightguide. The outcoupling elements couple light out of the lightguide at respective positions along the length of the lightguide. The outcoupling elements are oriented to direct the outcoupled light towards the target when the lens side is in opposing relation to the target.

The apparatus according to the first aspect may include one or more of the features summarized below.

The lightguide may be a light pipe, and the outcoupling elements may be surface indentations on the light pipe or bumps on a surface of the light pipe or holes in a wall of the light pipe. Alternatively, the lightguide may be an optical fiber having a core and a cladding surrounding the core, and the outcoupling elements may be depressions in the cladding that extend into the core of the optical fiber or radial protrusions on the core of the optical fiber that penetrate the cladding. Alternatively, the lightguide may be a light pipe, and the outcoupling elements may be refractive optical elements carried by the light pipe.

The lightguide may have a terminal end, where the length of the lightguide extends from the input end to the terminal end, and where the terminal end includes a reflective surface oriented to reflect light back into the lightguide. Alternatively, the lightguide may be formed as a closed loop, and the input end of the lightguide may be a portion of the closed loop. An input coupler may be optically coupled to the portion of the closed loop that forms the input end. The input coupler can couple light into the lightguide through the portion of the closed loop that forms the input end.

The support frame may include a frame front and at least one temple attached to the frame front, where the frame front has a lens mounting area to carry the lens and a channel to carry the lightguide and outcoupling elements, where the channel at least partially circumscribes a periphery of the lens mounting area.

The lightguide and outcoupling elements may be enclosed within the frame front. The frame front may include a frame side oriented to face in a same direction as the lens side. The frame front may include a plurality of apertures corresponding to the plurality of outcoupling elements, where each aperture opens to the frame side and is optically coupled to a respective one of the outcoupling elements. Alternatively, at least a portion of the frame front covering the outcoupling elements may be made of a material that is at least partially transparent to the light propagating along the length of the lightguide.

The at least one temple may carry an infrared light source, where an optical path is defined between an output end of the infrared light source and the input end of the lightguide. A window may be formed within the support frame and between the frame front and the at least one temple, where the optical path extends from the output end of the infrared light source to the input end of the lightguide through the window.

The lens may be a combiner lens.

In a second aspect, an eye tracking apparatus for tracking an eye of a subject may be summarized as including an apparatus to illuminate a target according to the first aspect and an infrared detector positioned and oriented to detect reflections of infrared light from the target.

In a third aspect, an eye tracking apparatus for tracking an eye of a subject may be summarized as including a support frame that carries a lens, an infrared illuminator, an infrared light source, and an infrared detector. The lens has a lens side that is positioned in opposing relation to the eye of the subject when the support frame is worn on the head of the subject. The infrared illuminator includes a lightguide that circumscribes at least a portion of a periphery of the lens.

The lightguide has an input end to receive infrared light and a length along which the received infrared light propagates. The infrared illuminator also includes a plurality of outcoupling elements spaced out along the length of the lightguide. The outcoupling elements are optically coupled to the lightguide to couple light out of the lightguide at respective positions along the length of the lightguide. The outcoupling elements are oriented to direct the outcoupled light towards the eye of the subject when the support frame is worn on the head of the subject. The infrared light source provides the infrared light that is received at the input end of the lightguide. The infrared detector is positioned and oriented to detect reflections of infrared light from the eye of the subject when the support frame is worn on the head of the subject.

The eye tracking apparatus according to the third aspect may include one or more of the features summarized below.

The support frame may include a frame front and at least one temple attached to the frame front, where the frame front has a lens mounting area to carry the lens and a channel to carry the infrared illuminator, where the channel at least partially circumscribes a periphery of the lens mounting area. The at least one temple may carry the infrared light source. The frame front may carry the infrared detector, or the at least one temple may carry the infrared detector.

The infrared illuminator may be enclosed within the frame front. The frame front may include a frame side oriented in a same direction as the lens side. At least a portion of the frame front covering the outcoupling elements may be made of a material that is at least partially transparent to the infrared light propagating along the length of the lightguide. Alternatively, the frame front may include a plurality of apertures corresponding to the plurality of outcoupling elements, where each aperture provides a path through which outcoupled light from a corresponding outcoupling element is directed out of the frame front.

The lens may be a combiner lens.

An infrared hologram that is responsive to infrared light and unresponsive to other light may be positioned to receive reflections of infrared light from the eye of the subject and redirect the reflections of the infrared light. The infrared detector may be oriented to receive the reflections of infrared light redirected by the infrared hologram.

The infrared hologram may be carried by the lens.

In a fourth aspect, a method of tracking a gaze position of an eye in a target space in a field of view of the eye may be summarized as including positioning a portion of a support frame carrying a lens and an infrared illuminator in opposing relation to the eye, the infrared illuminator comprising a lightguide at least partially circumscribing a periphery of the lens and a plurality of outcoupling elements spaced out along a length of the lightguide; generating infrared light; directing the infrared light into an input end of the lightguide, where the infrared light travels along the length of the lightguide; at a plurality of positions along the length of the lightguide corresponding to the plurality of outcoupling elements, coupling light out of the lightguide in a direction towards the eye; detecting reflections of infrared light from the eye; and determining the gaze position of the eye from the detected reflections of infrared light.

The foregoing general description and the following detailed description are exemplary of the invention and are intended to provide an overview or framework for understanding the nature of the invention as it is claimed. The accompanying drawings are included to provide further understanding of the invention and are incorporated in and constitute part of this specification. The drawings illustrate various embodiments of the invention and together with the description serve to explain the principles and operation of the invention.

BRIEF DESCRIPTION OF DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with portable electronic devices and head-worn devices have not been shown or described in detail to avoid unnecessarily obscuring descriptions of the embodiments. For the sake of continuity, and in the interest of conciseness, same or similar reference characters may be used for same or similar objects in multiple figures. For the sake of brevity, the term "corresponding to" may be used to describe correspondence between features of different figures. When a feature in a first figure is described as corresponding to a feature in a second figure, the feature in the first figure is deemed to have the characteristics of the feature in the second figure, and vice versa, unless stated otherwise.

In this disclosure, unless the context requires otherwise, throughout the specification and claims which follow, the word "comprise" and variations thereof, such as, "comprises" and "comprising" are to be construed in an open, inclusive sense, that is as "including, but not limited to."

In this disclosure, reference to "one implementation" or "an implementation" or to "one embodiment" or "an embodiment" means that a particular feature, structures, or characteristics may be combined in any suitable manner in one or more implementations or one or more embodiments.

In this disclosure, the singular forms "a," "an," and "the" include plural referents unless the content clearly dictates otherwise. It should also be noted that the term "or" is generally employed in its broadest sense, that is, as meaning "and/or" unless the content clearly dictates otherwise.

The headings and Abstract of the disclosure provided herein are for convenience only and do not interpret the scope or meaning of the embodiments or implementations.

Throughout this specification, the term "infrared" will be understood to include "near infrared" and will generally refer to a wavelength of light that is longer than the largest wavelength of light that is typically visible to the average human eye. Light that is visible to the average human eye, i.e., "visible light" herein, is generally in the range of 400 nm-700 nm. Thus, as used herein, the term "infrared" refers to a wavelength that is greater than 700 nm, up to 1 mm.

Figure 1:
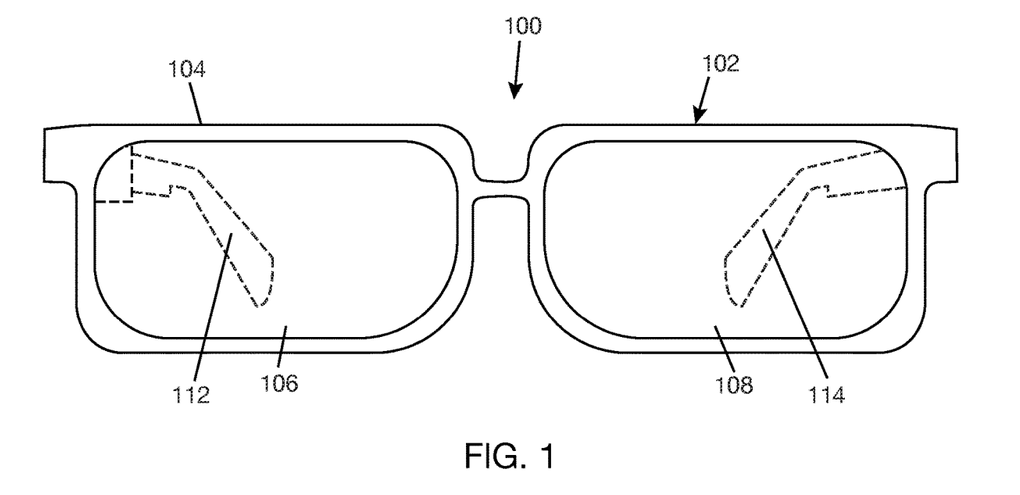
FIG. 1 is a front elevational view showing an eye tracking apparatus.

FIG. 1 shows an eye tracking apparatus 100 having the form of glasses (or eyeglasses). Eye tracking apparatus 100 may also be a wearable heads-up display having eye tracking capabilities. Eye tracking apparatus 100 includes a support frame 102 having a frame front 104 carrying a pair of lenses 106, 108. Support frame 102 also includes temples 112, 114 attached to opposite sides of frame front 104. Frame front 104 may be a single molded piece or may be formed from various molded pieces. Parts of frame front 104 may be integrally formed with front ends of temples 112, 114. Hence, the term "frame front" will generally refer to the front portion of support frame 102 that holds lenses 106, 108. In one example, support frame 102 carries optical and electronic components (not shown separately) for eye tracking. Support frame 102 may additionally carry optical and electronic components (not shown separately) to project display content to a display space in a field of view of the eye tracking apparatus 100. Support frame 102 may also carry communication components (not shown separately), such as antenna and the like.

In one implementation, either or both of lenses 106, 108 may be a combiner lens. The term "combiner lens" as used herein refers to a lens structure that includes one or more lenses in combination with one or more optical combiners, which may be free space combiners, e.g., holographic combiners, or substrate guided combiners, e.g., waveguide or lightguide combiners with input and output couplers. As examples, the optical combiner may be attached, embedded, or otherwise integrated with a lens to form the combiner lens, or the optical combiner may be sandwiched between two lenses to form the combiner lens. As an example, U.S. Provisional Application Nos. 62/754,339 and 62/734,798 ("Optical Combiner Lens for Wearable Heads-Up Display") disclose combiner lenses including lightguide combiners. In wearable heads-up displays, optical combiners are used to combine real world and virtual images. Therefore, the lens that is the combiner lens will generally be the lens through which the display will be viewed.

Figure 2:
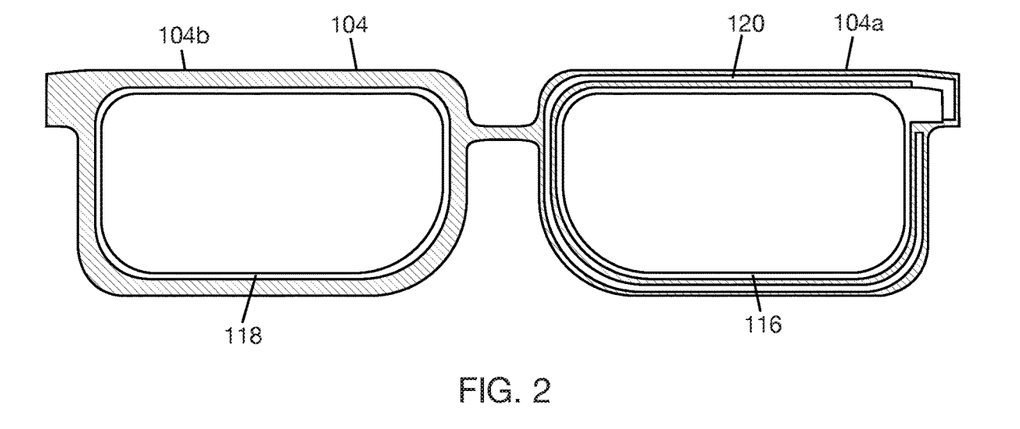
FIG. 2 is a cross-sectional view of a frame front of the eye tracking apparatus of FIG. 1.
Figure 3A:
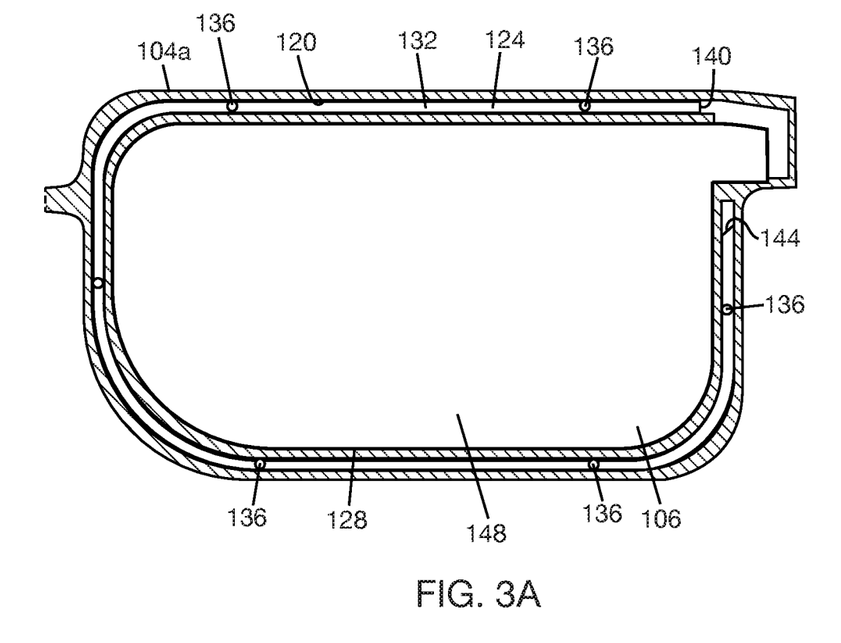
FIG. 3A is a cross-sectional view of a portion of the frame front of FIG. 2 with an infrared illuminator disposed in a channel in the frame front portion.

FIG. 2 shows a cross-section of frame front 104 according to one implementation. Frame front 104 includes lens mounting areas 116, 118, such as grooves, to hold edges of lenses 106, 108 (in FIG. 1), respectively. A channel 120 may be formed in the portion 104a of frame front 104 including lens mounting area 116 to hold an infrared illuminator (not shown). In alternate implementations, channel 120 could be formed in the portion 104b of frame front 104 including lens mounting area 118. The choice of where to include channel 120 on frame front 104 depends on which eye of the subject (or user) will be tracked. In the example of FIG. 2, channel 120 is disposed adjacent to lens mounting area 116 and circumscribes at least a portion of lens mounting area 116, e.g., at least 50% of a periphery of lens mounting area 116 or at least two-thirds of a periphery of lens mounting area 116. FIG. 3A shows an infrared illuminator 124 disposed in channel 120 and lens 106 mounted in lens mounting area 116 (in FIG. 2). Infrared illuminator 124 is in the form of a loop circumscribing at least a portion of the periphery of 128 of lens 106. In general, at least 50% of the periphery 128 of lens 106 is circumscribed by infrared illuminator 128. More typically, at least two-thirds of the periphery 128 of lens 106 is circumscribed by infrared illuminator 128. An alternative to disposing infrared illuminator 124 in channel 120 is to mount infrared illuminator 124 on periphery 128 of lens 106, where infrared illuminator 124 will thereby circumscribe at least a portion of the periphery 128 of lens 106. In this case, lens mounting area 116 (in FIG. 2) will need to accommodate infrared illuminator 124.

Infrared illuminator 124 includes a lightguide 132 and outcoupling elements 136. Lightguide 132 has an input end 140 to receive light from a light source (not shown), a terminal end 144, and properties to propagate the received light from the input end 140 towards the terminal end 144. The properties may be material properties or structures to guide light, e.g., by total internal reflection for light entering at angles that are equal to or greater than an associated critical angle. In one implementation, lightguide 132 receives infrared light at input end 140 and has properties to propagate the received infrared light. Outcoupling elements 136 are positioned on and spaced out along a length of lightguide 132 between input end 140 and terminal end 144 to couple light out of lightguide 132. Outcoupling elements 136 are positioned on a side of lightguide 132 that is oriented to face in the same direction as an eye-facing lens side 148 of lens 106 so as to illuminate a target, such as an eye, that is positioned in opposing relation to eye-facing lens side 148. Outcoupling elements 136 may be attached to lightguide 132 or integrally formed with lightguide 132. In general, outcoupling elements 136 are optically connected to lightguide 132 or a portion of lightguide 132 carrying light. Terminal end 144 may be a reflective surface and/or oriented to reflect light back into lightguide 132. Alternatively, an optical beam dump (not shown) may be provided in channel 120 proximate terminal end 144 to absorb excess light exiting terminal end 144.

Figure 3B:
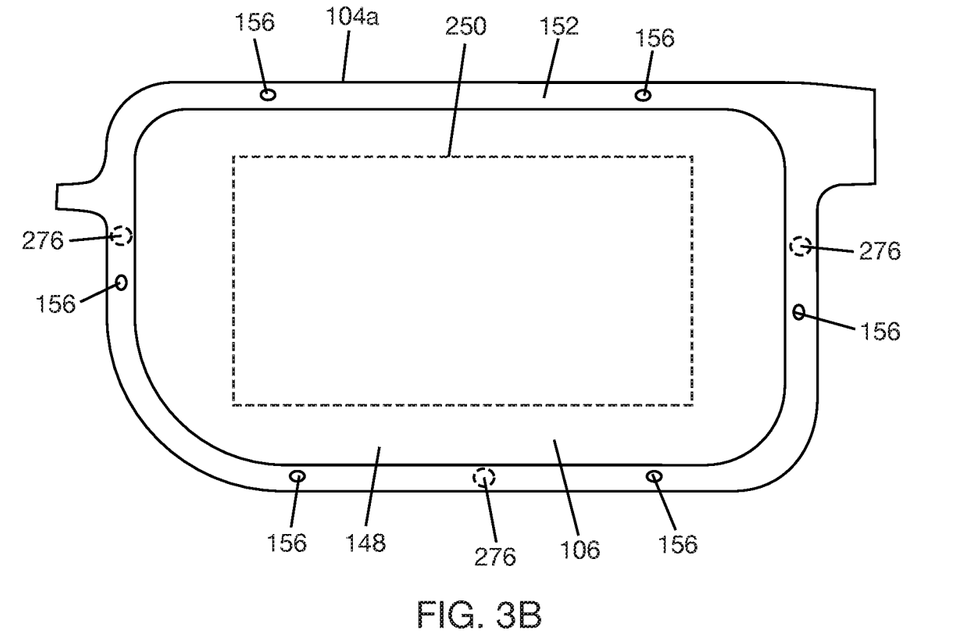
FIG. 3B is a rear elevational view of the frame front portion of FIG. 3A.

In one implementation, infrared illuminator 124 is enclosed within frame front portion 104a such that infrared illuminator 124 is not visible from an eye side of frame front portion 104a. FIG. 3B shows an eye-facing frame side 152 of frame front portion 104a, which is the side facing the same direction as eye-facing lens side 148. In one example, apertures 156 may be formed in frame front portion 104a in positions corresponding to outcoupling elements 136 to serve as paths through which light from respective outcoupling elements 136 can exit frame front portion 104a. Apertures 156 open to eye-facing frame side 152 and extend into frame front portion 104a and are optically coupled to outcoupling elements 136, i.e., there is an optical path through which light can move from each outcoupling element 136 to a respective aperture 156. Apertures 156 may be empty or may be filled or covered with material that is transparent to infrared light. The filler material, if used, may be opaque to visible light so that openings 156 are less visible to the eye. Alternatively, frame front portion 104a, or a portion of frame front portion 104a covering outcoupling elements 136 (in FIG. 2), may be made from material that is transparent to infrared light but opaque or translucent to visible light, which would allow infrared light from outcoupling elements 136 to pass through frame front portion 104a without the need for apertures 156.

Returning to FIG. 3A, the number of outcoupling elements 136 and the spacing between outcoupling elements 136 on lightguide 132 may be selected to achieve a uniform distribution of light along periphery 128 of lens 106. As a non-limiting example, there may be six or more outcoupling elements 136 on lightguide 132. Lightguide 132 may be an optical fiber having a core and cladding or may be a light pipe. The light pipe may be a transparent solid that propagates light entering at or greater than a critical angle by total internal reflection or may be a hollow structure that contains light with reflective surface(s). Lightguide 132 may be flexible so that it can be shaped to generally follow the contour of channel 120, or lightguide 132 may be pre-formed with the desired shape that follows the contour of channel 120. Outcoupling elements 136 could take on various forms, such as surface discontinuities on lightguide 120, refractive or diffractive optical elements attached to lightguide 120, and the like.

Figure 4A:
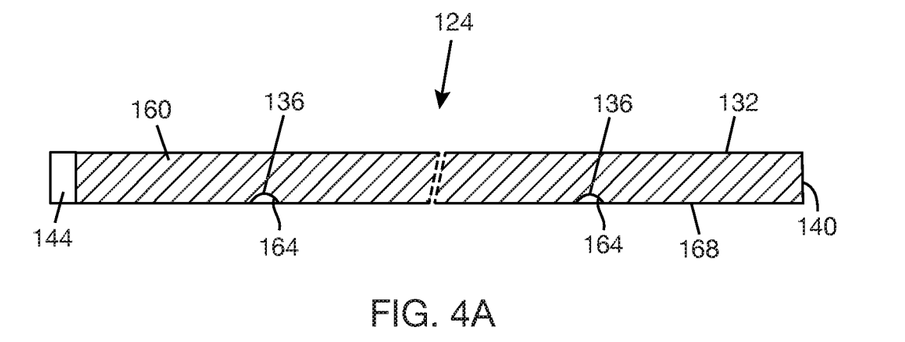
FIG. 4A is a cross-sectional view of an infrared illuminator including a light pipe and surface indentations on the light pipe according to one example.
Figure 4B:
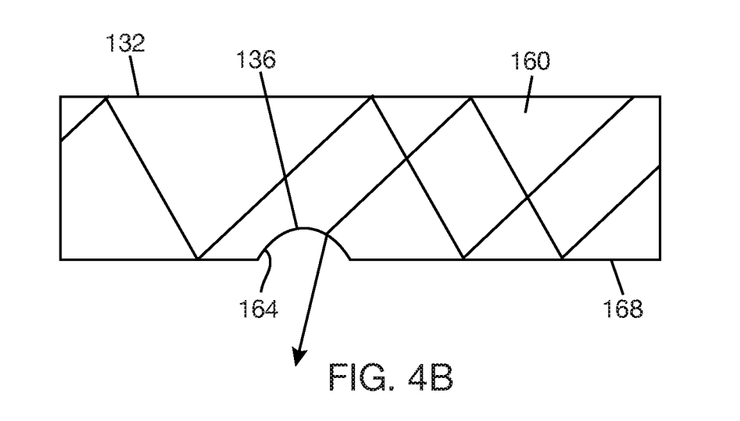
FIG. 4B is a schematic illustrating light coupled out of a light pipe through a surface indentation on the light pipe.

FIG. 4A shows one example of infrared illuminator 124 where lightguide 132 is a light pipe 160. In this example, light pipe 160 is a solid pipe that is transparent to infrared light. Light fed into light pipe 160 at input end 140 at angles that are equal to or greater than an associated critical angle will travel towards terminal end 144 by total internal reflection. Where infrared illuminator 124 is enclosed within frame front portion 104a (in FIG. 3A), the material of light pipe 160 can be selected to have a refractive index that is higher than that of the material of frame front portion 104a (or the material of the portion of frame front portion 104a surrounding infrared illuminator 124). Surface indentations 164 on surface 168 of light pipe 160 provide the outcoupling elements 136 of infrared illuminator 124. Surface indentations 164 introduce discontinuities at surface 168 of light pipe 160 that disrupt propagation of light through light pipe 160. As light propagates through light pipe, as shown in FIG. 4B, a fraction of the light will encounter each surface indentation 164, which will redirect the light out of light pipe 160. In the example of FIGS. 4A and 4B, surface indentations 164 are dimples. However, other types of surface indentations besides dimples, such as grooves or notches, may be formed in surface 168 to function as outcoupling elements 136.

Figure 5:
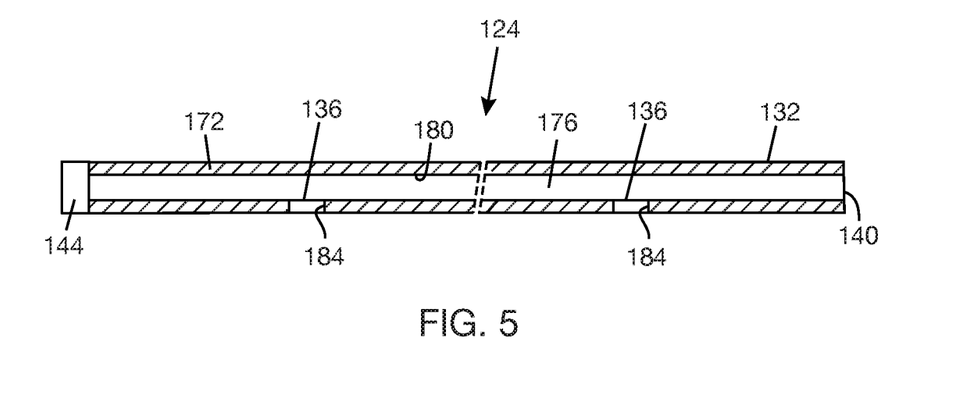
FIG. 5 is a cross-sectional view of an infrared illuminator including a light pipe and through-holes in the wall of the light pipe according to another example.

FIG. 5 shows another example of infrared illuminator 124 where lightguide 132 is a light pipe 172. In this example, light pipe 172 is a hollow pipe with a bore 176 and a reflective surface 180 surrounding the bore 176. Apertures 184 formed in a wall of light pipe 172 provide outcoupling elements 136. Apertures 184 are through-holes that penetrate reflective surface 180 and are optically connected to bore 176. Light fed into light pipe 172 at input end 140 at angles that are equal to or greater than an associated critical angle will travel towards terminal end 144 by total internal reflection and will be contained in bore 176 by reflective surface 180. Apertures 184 introduce discontinuities at the reflective surface 180 that disrupt containment of light in bore 176 by reflective surface 180, allowing light to exit light pipe 172 at the point of disruption.

Figure 6A:
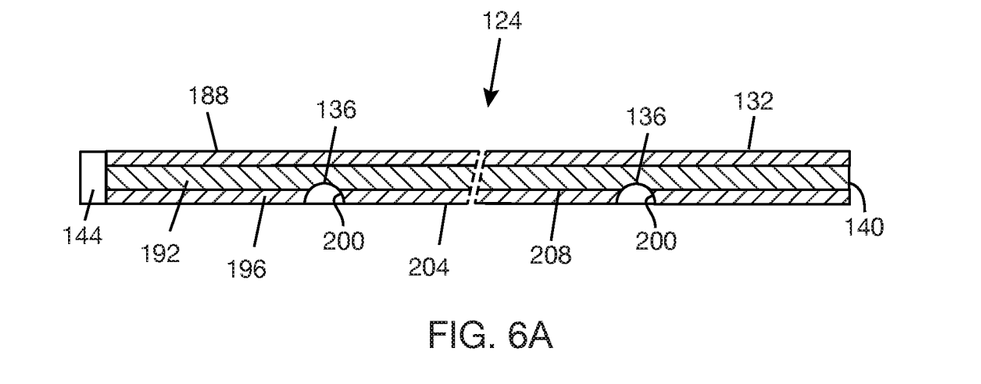
FIG. 6A is a cross-sectional view of an infrared illuminator including an optical fiber and depressions in the optical fiber according to another example.
Figure 6B:
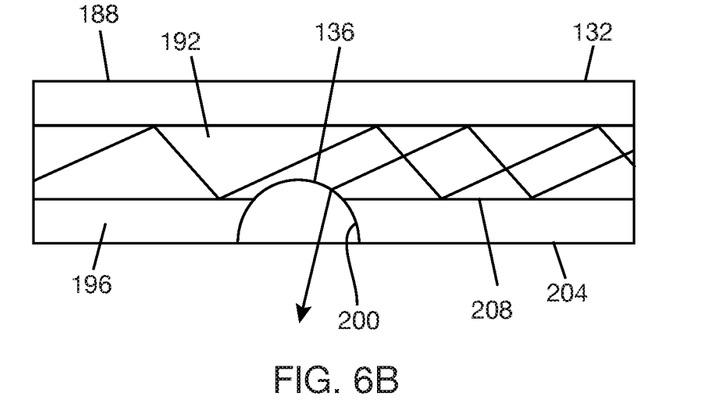
FIG. 6B is a schematic illustrating light coupled out of an optical fiber through a depression in the optical fiber.

FIG. 6A shows another example of infrared illuminator 124 where lightguide 132 is an optical fiber 188 having a core 192 and a cladding 196 surrounding core 192. The refractive index of core 192 is higher than the refractive index of cladding 196, which allows light to propagate along core 192 by total internal reflection. Depressions 200 formed in optical fiber 188 provide outcoupling elements 132 of infrared illuminator 124. Depressions 200 extend from an outer surface 204 of optical fiber 188, through cladding 196, into core 192. Depressions 200 create discontinuities at the boundary 208 between core 192 and cladding 196. Light coupled into optical fiber 188 from input end 140 at angles that are equal to or greater than an associated critical angle will be guided along core 192 towards terminal end 144 by total internal reflection. At each depression 200, a fraction of the light propagating through core 192 will encounter the discontinuity created by the depression 200 and will be refracted out of optical fiber 188, as shown in FIG. 6B. The remaining fraction of light will continue to propagate through core 192 until reaching the next depression 200 or terminal end 144.

Figure 7A:
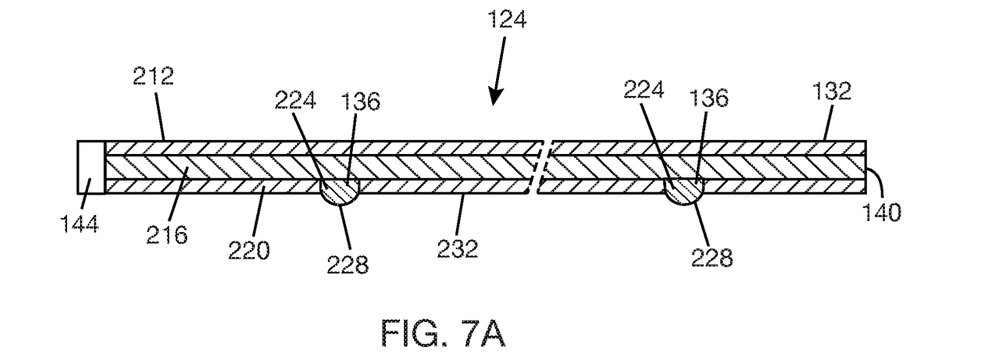
FIG. 7A is a cross-sectional view of an infrared illuminator including an optical fiber and protrusions on the optical fiber according to another example.
Figure 7B:
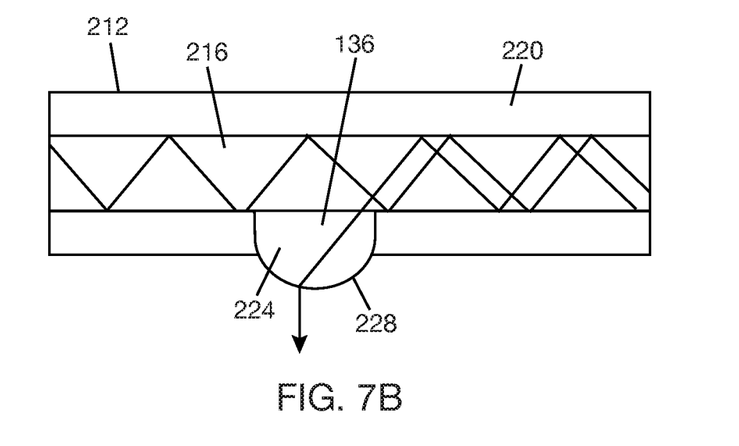
FIG. 7B is a schematic view illustrating light coupled out of an optical fiber through a protrusion on the optical fiber.

FIG. 7A shows another example of infrared illuminator 124 where lightguide 132 is an optical fiber 212 having a core 216 and a cladding 220 surrounding the core 216. The refractive index of core 216 is higher than the refractive index of cladding 220, which allows light to propagate along core 216 by total internal refection. Protrusions 224 on core 216 provide outcoupling elements 136 of infrared illuminator 124. Protrusions 224 extend radially from core 216, penetrating cladding 220 and emerging as bumps 228 on an outer surface 232 of optical fiber 212. Protrusions 224 may be integrally formed with core 216 or may be inserts mounted in holes that extend from outer surface 232 of optical fiber 212, through cladding 220, to core 216 of optical fiber 212. In general, protrusions 224 are optically connected to core 216, e.g., by being formed integrally with core 216, by being in physical contact with core 216, or by being attached to core 216 by an optical adhesive. Protrusions 224 may be index matched to core 216. Bumps 228 formed by ends of protrusions 224 may be convex surfaces, i.e., bulging outwardly relative to outer surface 232 of optical fiber 212. Light is fed into core 216 from input end 140. As light propagates through core 216 towards terminal end 144, a fraction of the light will enter each protrusion 224, as shown in FIG. 7B, and will be refracted at the boundary of the respective bump 228 in a direction outward of optical fiber 212.

Figure 8:
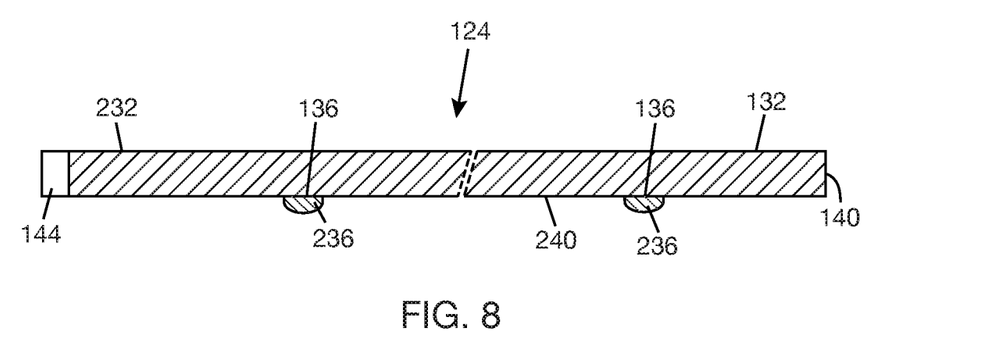
FIG. 8 is a cross-sectional view of an infrared illuminator including a light pipe and bumps on the light pipe according to another example.

FIG. 8 shows another example of infrared illuminator 124 where lightguide 132 is a light pipe 232. In this example, light pipe 232 is a solid pipe that is transparent to infrared light. Infrared light fed into input end 140 at angles that are equal to or greater than an associated critical angle will travel along the length of light pipe 232 and towards terminal end 144 by total internal reflection. Where infrared illuminator 124 is enclosed within frame front portion 104a (in FIG. 3A), the material of light pipe 232 can be selected to have a refractive index that is higher than that of the material of frame front portion 104a (or the material of the portion of frame front portion 104a surrounding infrared illuminator 124). Refractive optical elements 236, e.g., lenses, on light pipe 232 provide outcoupling elements 136 of infrared illuminator 124. Refractive optical elements 236 may be attached to surface 240 of light pipe 232. While light is traveling through light pipe 232, at least a fraction of light incident on each refractive optical element 236 from inside light pipe 232 will be coupled out of light pipe 232.

Figure 9:
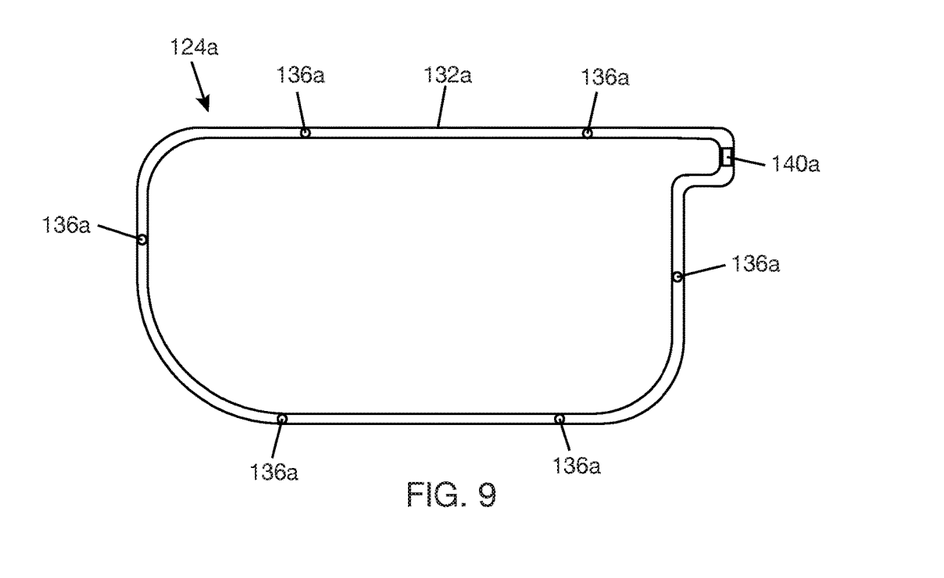
FIG. 9 is a schematic illustrating an infrared illuminator including a lightguide in a closed loop form.

Infrared illuminator 124 has been described above as including a lightguide 132 having an input end 140 and terminal end 144. In an alternate embodiment, lightguide 132 may be formed as a closed loop and may not have a terminal end. The input end may be a portion of the closed loop that is optically connected to an input coupler. FIG. 9 shows an example of infrared illuminator 124a where lightguide 132a is a closed loop. Input coupler 140a is optically connected to lightguide 132a to couple light into lightguide 132a. Input coupler 140a may be, for example, a hologram, a volume diffraction grating, a surface relief grating, a transmission grating, or a reflecting grating. Outcoupling elements 136a are spaced out along the length of the closed loop. Lightguide 132a and outcoupling elements 136a may have any of the structures described above for lightguide 132 and outcoupling elements 136, with the exception that lightguide 132a is in the form of a closed loop. Light, e.g., infrared light, will be coupled into lightguide 132a through input coupler 140a and out of lightguide 132a through outcoupling elements 136a.

Figure 10A:
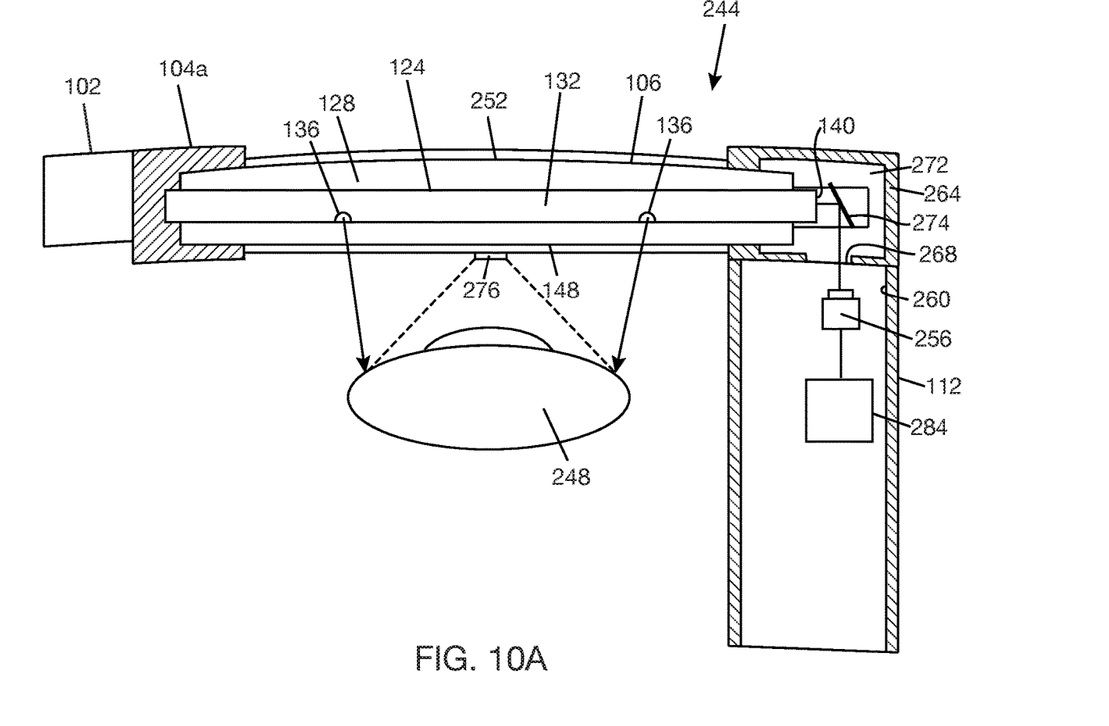
FIG. 10A is a schematic view of an eye tracking system including a frame front carrying an infrared illuminator and lens and an infrared detector positioned on an eye-facing side of the frame front according to one example.
Figure 10B:
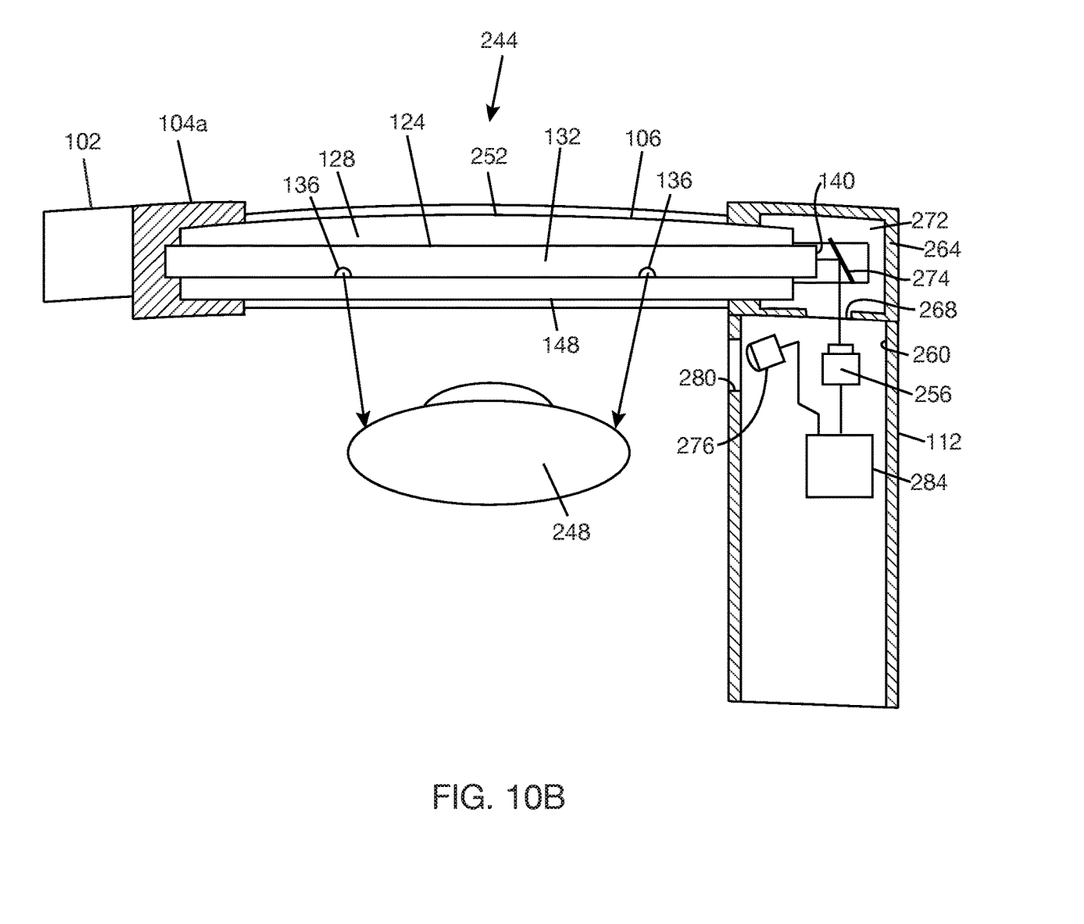
FIGS. 10B and 10C are schematic views of an eye tracking system including a frame front carrying an infrared illuminator and lens and an infrared detector positioned in a temple attached to the frame front according to other examples.
Figure 10C:
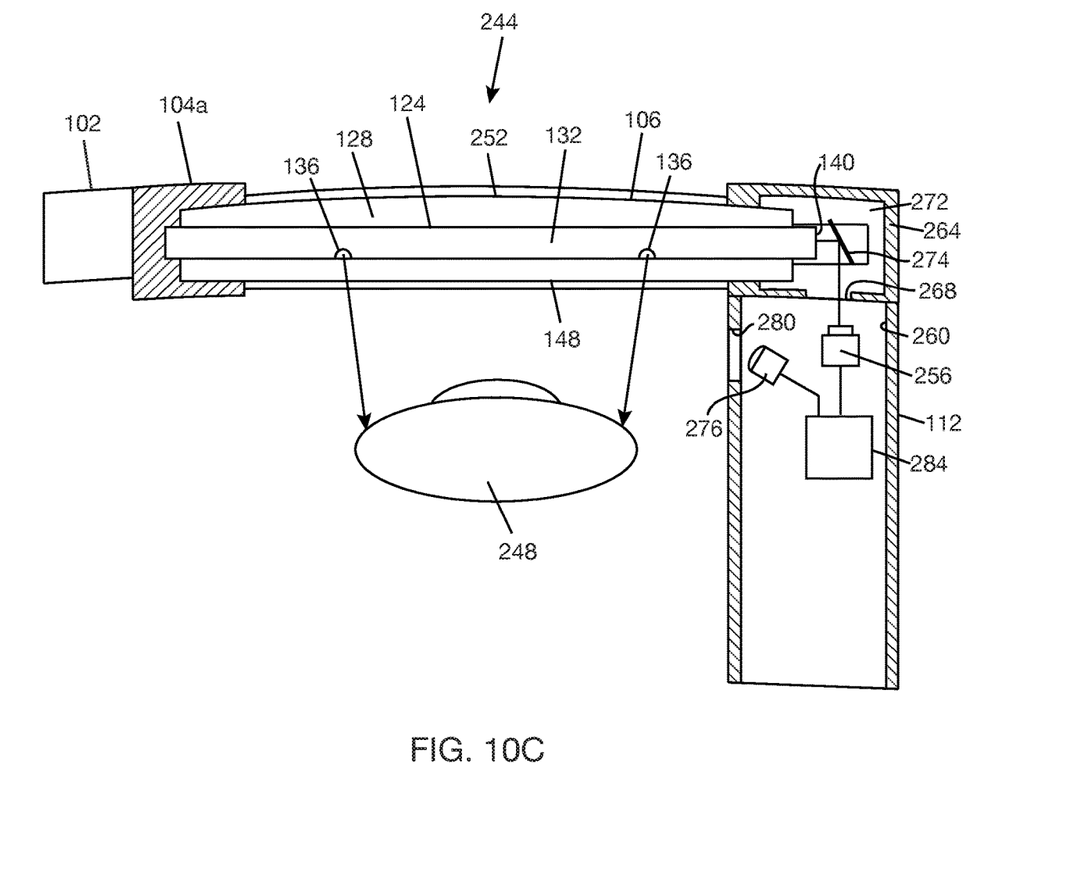

FIGS. 10A-10C show an eye tracking system 244 corresponding to the eye tracking apparatus 100 in FIG. 1. Eye tracking system 244 tracks a gaze position of an eye 248 in a target space in a field of view of eye 248. Eye tracking system 244 includes frame front portion 104a carrying lens 106 and infrared illuminator 124. Eye-facing lens side 148 of lens 106 faces eye 248 whose gaze position is to be tracked. World-facing lens side 252 of lens 106 is opposite to eye-facing lens side 148 and faces the world, e.g., the environment in front of eye 248. Infrared illuminator 124 circumscribes at least a portion of periphery 128 of lens 106, as previously described. Infrared illuminator 124 may be carried by frame front portion 104a, as previously described. Infrared illuminator 124 includes lightguide 132 and outcoupling elements 136, as previously described. Infrared illuminator 124 is arranged to illuminate eye 248 with infrared light. In general, this includes positioning outcoupling elements 136 on a side of lightguide 132 that faces in the same direction as eye-facing lens side 148 of lens 106.

Eye tracking system 244 includes an infrared light source 256, e.g., an infrared light emitting diode (LED) or infrared laser diode, to generate infrared light. Lightguide 132 receives infrared light from infrared light source 256. In one example, infrared light source 256 is disposed in a cavity 260 in temple 112 attached to end 264 of frame front portion 104a. A window 268 may be formed between a cavity 272 in end 264 of frame front portion 104a and cavity 260 in temple 112. Input end 140 of lightguide 132 may be accessible from temple 112 through window 268 and cavity 272. In one example, light is directed from infrared light source 256, through window 268, to input end 140 of lightguide 132. One or more optical elements, e.g., mirror 274, may be used to align the infrared light from infrared light source 256 with input end 140 of lightguide 132. Alternatively, if there is sufficient room in cavity 272 of frame front portion 104a, infrared light source 256 may be disposed in cavity 272, and the output end of infrared light source 256 may be aligned with input end 140 of lightguide 132. Alternatively, input end 140 of lightguide 132 may be extended into cavity 260 or near window 268 and aligned with the output end of infrared light source 256. In some cases, input end 140 may be physically attached to the output end of infrared light source 256.

Eye tracking system 244 includes at least one infrared detector 276 to capture an image of the eye. Infrared detector 276 may be, for example, an array of photodetectors that are responsive to infrared light, a complementary metal-oxide semiconductor (CMOS) camera or charge-coupled device (CCD) camera having an array of sensors that are responsive to light in the infrared range, or other image sensor. In the example shown in FIG. 10A, infrared detector 276 is positioned on eye-facing side of frame front portion 104a to directly capture an image of eye 248. (FIG. 3B shows examples of various positions of infrared detector(s) 276 on eye-facing side of frame front portion 104a. In general, infrared detector 276 should be positioned where it is unlikely that eyelashes would occlude the image captured by infrared detector 276.) In the example shown in FIGS. 10B and 10C, infrared detector 276 is disposed in cavity 260 in temple 112. Temple 112 may include a window 280 through which infrared detector 276 may capture an image of eye 248 (or detect reflections of infrared light from eye 248). In the example shown in FIG. 10B, infrared detector 276 is oriented towards eye 248 to capture an image of eye 248. In the example shown in FIG. 10C, infrared detector 276 is oriented towards lens 106 to capture an image of eye 148 from lens 106.

In the example of FIG. 10C, lens 106 may be a combiner lens including an infrared hologram (illustrated at 250 in FIG. 3B) to redirect reflections of infrared light from eye 248 to infrared detector 276. The infrared hologram is a hologram that is responsive to infrared light and unresponsive to other light. In one example, the infrared hologram is a hologram that is responsive to infrared light, e.g., infrared light within a particular range emitted by infrared light source 256, and unresponsive to visible light. Responsive to infrared light means that the infrared hologram redirects at least a portion of the infrared light, where the magnitude of the portion depends on the playback efficiency of the infrared hologram. Unresponsive to visible light mean that the infrared hologram transmits the visible light, generally without modifying the visible light. The infrared hologram may be separate from other optical combiners in the combiner lens used for display purposes. U.S. Provisional Application 62/734,798 ("Optical Combiner Lens for Wearable Heads-Up Display") discloses an example of a combiner lens including an infrared hologram. The disclosure of U.S. Provisional Application 62/734,798 is incorporated herein by reference.

Figure 11:
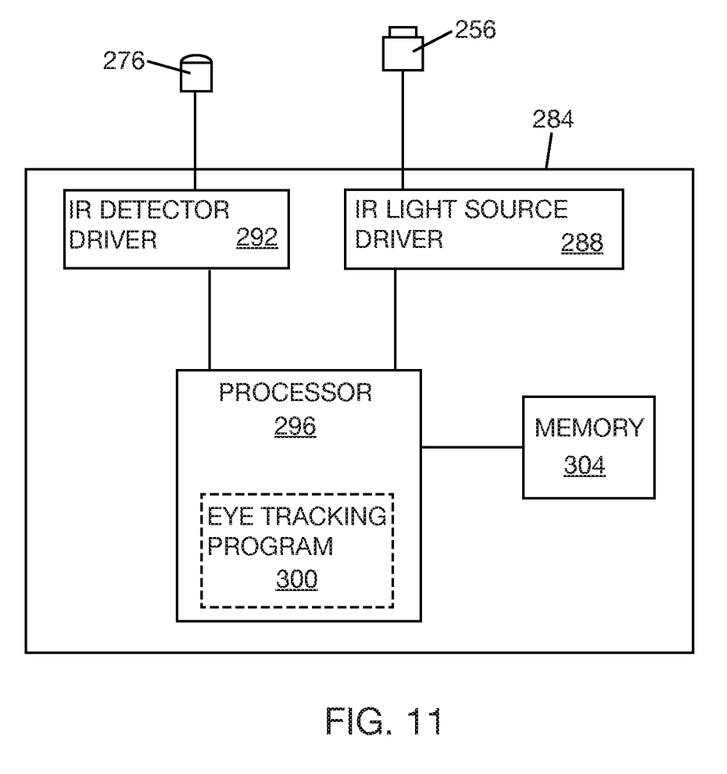
FIG. 11 is a block diagram of an eye tracking engine.

Eye tracking system 244 may include an eye tracking engine 284 that is communicatively coupled to infrared light source 256 and infrared detector 276. Referring to FIG. 11, eye tracking engine 284 may include an infrared light source driver 288 to operate infrared light source 256 and an infrared detector driver 292 to receive the output of infrared detector 276. Eye tracking engine 284 may include a processor 296 that is communicatively coupled to infrared detector driver 292 and infrared light source driver 288 to provide controls and/or receive data. Processor 296 may be a programmed computer that performs computational operations. For example, processor 296 may be a central processing unit (CPU), a microprocessor, a controller, an application specific integrated circuit (ASIC), a system on chip (SOC), or a field-programmable gate array (FPGA).

An eye tracking program 300 (e.g., processor-executable instructions) may be stored in memory 304 and executed by processor 296. Eye tracking program 300 includes logic to receive infrared detector data (captured image or detected reflections of infrared light) from infrared detector driver 292 and compute gaze position from the infrared detector data. In one example, eye tracking program 300 may determine a glint center position of the eye from the infrared detector data and transform the glint center position from the detector space to a target space in a field of view of the eye using a mapping function that transforms coordinates from the detector space to the target space. In another example, eye tracking program 300 may determine a glint center position and a pupil center position of the eye from the infrared detector data, compute a glint-pupil vector from the glint center position and the pupil center position, and transform the glint-pupil vector to the target space in the field of view of the eye using a mapping function that transforms glint-pupil vectors from the detector space to the target space. The mapping function(s) may be determined beforehand during a calibration process.

Returning to FIGS. 10A-10C, to track a gaze position of eye 248 in a target space in a field of view of eye 248, lens 106 and infrared illuminator 124 are positioned in opposing relation to eye 248 as shown. Frame front portion 104a of support frame 102 may be used to support lens 106 and infrared illuminator 124 in front of eye 248. Infrared light source 256 is operated to generate infrared light, which is directed to input end 140 of lightguide 128 of infrared illuminator 124. Infrared light fed into input end 140 of lightguide 128 will travel along the length of lightguide 128. At each outcoupling element 136 on lightguide 128, some of the infrared light traveling along the length of lightguide 128 will be coupled out of lightguide 128 and directed to eye 248, illuminating eye 248. Reflections of infrared light from eye 248 as a result of illuminating eye 248 are detected by infrared detector 276. An image of eye 248 can be constructed from the output of infrared detector 276 and used to determine a gaze position of eye 248 as described above. For example, the glint center position and/or pupil center position can be extracted from the image and used to determine the gaze position of eye 248 in the target space. Although not shown, a display projector can be integrated in eye tracking system 244 to form a wearable heads-up display. The target space in which the gaze position of eye 248 is tracked can be a space in which the display projector forms a display UI.

Although illuminator 124 (124a) has been described as an infrared illuminator, in some cases, illuminator 124 (124a) may emit other types of light, such as visible light. That is, in some cases, lightguide 132 (132a) may receive light other than infrared light through its input end, and outcoupling elements 136 (136a) may couple out light other than infrared light at their respective positions along lightguide 132 (132a). If infrared illuminator 124 (124a) is to be used as a visible light illuminator, for example, the materials or structure of lightguide 132 (132a) and outcoupling elements 136 (136a) should be selected to permit transmission of the visible light. In other respects, the structure of the visible light illuminator can be the same as described above and in FIGS. 1-9 for infrared illuminator 124 (124a).

The above description of illustrated embodiments, including what is described in the Abstract of the disclosure, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art. The teachings provided herein of the various embodiments can be applied to other portable and/or wearable electronic devices, not necessarily the exemplary wearable electronic devices generally described above.

The invention claimed is:

1. An apparatus to illuminate a target, the apparatus comprising:
   a support frame;
   a lens carried by the support frame, the lens having a lens side that is to be positioned in opposing relation to the target;
   a lightguide carried by the support frame and comprising an optical fiber having a core and a cladding surrounding the core, the lightguide circumscribing at least a portion of the periphery of the lens, the lightguide having an input end to receive light and a length along which the received light propagates; and
   a plurality of outcoupling elements spaced out along the length of the lightguide, the outcoupling elements optically coupled to the lightguide to couple light out of the lightguide at respective positions along the length of the lightguide, the outcoupling elements oriented to direct the outcoupled light towards the target when the lens side is in opposing relation to the target, wherein the outcoupling elements are depressions in the cladding that extend into the core of the optical fiber or radial protrusions on the core of the optical fiber that penetrate the cladding.

2. The apparatus of claim 1, wherein the lightguide comprises a light pipe, and wherein the outcoupling elements are surface indentations on the light pipe, bumps on a surface of the light pipe, or holes in a wall of the light pipe.

3. The apparatus of claim 1, wherein the lightguide is a light pipe, and wherein the outcoupling elements are refractive optical elements carried by the light pipe.

4. The apparatus of claim 1, wherein the lightguide has a terminal end, wherein the length of the lightguide extends from the input end to the terminal end, and wherein the terminal end includes a reflective surface oriented to reflect light back into the lightguide.

5. The apparatus of claim 1, wherein the lightguide is formed as a closed loop and the input end of the lightguide is a portion of the closed loop, and further comprising an input coupler optically coupled to the portion of the closed loop, the input coupler to couple light into the lightguide through the portion of the closed loop.

6. The apparatus of claim 1, wherein the support frame comprises a frame front and at least one temple attached to the frame front, the frame front having a lens mounting area to carry the lens and a channel to carry the lightguide and outcoupling elements, and wherein the channel at least partially circumscribes a periphery of the lens mounting area.

7. The apparatus of claim 6, wherein the lightguide and outcoupling elements are enclosed within the frame front.

8. The apparatus of claim 7, wherein the frame front includes a frame side oriented to face in a same direction as the lens side, wherein the frame front includes a plurality of apertures corresponding to the plurality of outcoupling elements, and wherein each aperture opens to the frame side and is optically coupled to a respective one of the outcoupling elements.

9. The apparatus of claim 7, wherein at least a portion of the frame front covering the outcoupling elements is made of a material that is at least partially transparent to the light propagating along the length of the lightguide.

10. The apparatus of claim 6, further comprising an infrared light source carried by the at least one temple, wherein an optical path is defined between an output end of the infrared light source and the input end of the lightguide.

11. The apparatus of claim 10, further comprising a window formed within the support frame and between the frame front and the at least one temple, wherein the optical path extends from the output end of the infrared light source to the input end of the lightguide through the window.

12. The apparatus of claim 1, wherein the lens is a combiner lens.

13. The apparatus of claim 1, wherein the outcoupling elements are depressions in the cladding that extend into the core of the optical fiber.

14. The apparatus of claim 1, wherein the outcoupling elements are radial protrusions on the core of the optical fiber that penetrate the cladding.

15. An eye tracking apparatus for tracking an eye of a subject, comprising:
 a support frame that in use is worn on a head of the subject, the support frame having a frame front and at least one temple attached to the frame front;
 a lens carried by the frame front, the lens having a lens side that is positioned in opposing relation to the eye of the subject when the support frame is worn on the head of the subject;
 an infrared illuminator carried by the frame front, the infrared illuminator to illuminate the eye of the subject when the support frame is worn on the head of the subject, the infrared illuminator comprising:
 a lightguide circumscribing at least a portion of a periphery of the lens, the lightguide having an input end to receive infrared light, a length along which the received infrared light propagates, and an optical fiber having a core and a cladding surrounding the core; and
 a plurality of outcoupling elements spaced out along the length of the lightguide, the outcoupling elements optically coupled to the lightguide to couple light out of the lightguide at respective positions along the length of the lightguide, the outcoupling elements oriented to direct the outcoupled light towards the eye of the subject when the support frame is worn on the head, wherein the outcoupling elements are depressions in the cladding that extend into the core of the optical fiber or radial protrusions on the core of the optical fiber that penetrate the cladding;
 an infrared light source carried by the at least one temple, the infrared light source to provide the infrared light that is received at the input end of the lightguide, wherein an optical path is defined within the support frame and between an output end of the infrared light source and the input end of the lightguide; and
 an infrared detector carried by the support frame, the infrared detector positioned and oriented to detect reflections of infrared light from the eye of the subject when the support frame is worn on the head of the subject.

16. The eye tracking apparatus of claim 15, wherein the frame front has a lens mounting area to carry the lens and a channel to carry the infrared illuminator, and wherein the channel at least partially circumscribes a periphery of the lens mounting area.

17. The eye tracking apparatus of claim 15, wherein the lens is a combiner lens.

18. The eye tracking apparatus of claim 15, further comprising an infrared hologram that is responsive to infrared light and unresponsive to other light, the infrared hologram positioned to receive reflections of infrared light from the eye of the subject and redirect the reflections of the infrared light, wherein the infrared detector is positioned and oriented to receive the reflections of infrared light redirected by the infrared hologram.

19. The eye tracking apparatus of claim 18, wherein the infrared hologram is carried by the lens.

20. A method of tracking a gaze position of an eye in a target space in a field of view of the eye, comprising:
 positioning a portion of a support frame carrying a lens and an infrared illuminator in opposing relation to the eye, the infrared illuminator comprising a lightguide at least partially circumscribing a periphery of the lens, the lightguide including an optical fiber having a core and a cladding surrounding the core, and a plurality of outcoupling elements spaced out along a length of the lightguide, wherein the outcoupling elements are depressions in the cladding that extend into the core of the optical fiber or radial protrusions on the core of the optical fiber that penetrate the cladding;
 generating infrared light;
 directing the infrared light into an input end of the lightguide, wherein the infrared light travels along the length of the lightguide;
 at a plurality of positions along the length of the lightguide corresponding to the plurality of outcoupling elements, coupling light out of the lightguide in a direction towards the eye;
 detecting reflections of infrared light from the eye; and
 determining the gaze position of the eye from the detected reflections of infrared light.

* * * * *